United States Patent [19]
Amidon et al.

[11] Patent Number: 5,229,131
[45] Date of Patent: Jul. 20, 1993

[54] PULSATILE DRUG DELIVERY SYSTEM

[75] Inventors: Gordon L. Amidon; Glen D. Leesman, both of Ann Arbor, Mich.

[73] Assignee: University of Michigan, Ann Arbor, Mich.

[21] Appl. No.: 771,895

[22] Filed: Oct. 7, 1991

Related U.S. Application Data

[63] Continuation of Ser. No. 475,644, Feb. 5, 1990, abandoned.

[51] Int. Cl.$^5$ .............................................. A61K 9/48
[52] U.S. Cl. .................... 424/451; 424/464; 424/473; 424/480
[58] Field of Search .................. 424/473, 451, 464

[56] References Cited

U.S. PATENT DOCUMENTS

| | | | |
|---|---|---|---|
| 4,773,907 | 9/1988 | Urquhart | 424/467 |
| 4,777,049 | 10/1988 | Magruder | 424/457 |
| 4,783,337 | 8/1988 | Wong | 424/468 |

Primary Examiner—Thurman K. Page
Assistant Examiner—D. Gabrielle Phelan
Attorney, Agent, or Firm—Rohm & Monsanto

[57] ABSTRACT

A drug delivery system for administering a drug in controlled pulse doses to an aqueous environment in the body of a living being has one or more, and preferably less than ten, individual drug-containing subunits in a unitary drug depot, such as a tablet or capsule. The individual subunits are designed to dissolve at different sites and/or times in the gastrointestinal tract to release pulse doses of drug into the portal system in an analogous manner to the rate of release from an immediate release dosage form administered according to an appropriate dosing schedule. The dissolution time of the individual subunits can be controlled by several methods including the provision of pH-sensitive enteric coatings and permeability-controlled coatings. The drug delivery system has significant advantages for the oral administration of first-pass metabolized drugs which exhibit a non-linear relationship between input rate of the drug into the portal system and bioavailability.

18 Claims, 5 Drawing Sheets

PULSATILE DRUG DELIVERY SYSTEM

This invention was sponsored, in part, by the Department of Health and Human Services under Small Business Innovation Research Program Grant No. 1 R43 GM 37856-01, and therefore, the government of the United States of America may have certain rights in this invention.

This application is a continuation of application Ser. No. 07/475,644 filed Feb. 5, 1990, now abandoned.

BACKGROUND OF THE INVENTION

This invention relates generally to drug delivery systems, and more particularly, to a controlled release drug delivery system which is particularly suited for use with first-pass metabolized drugs and which delivers pulsed doses at predetermined time intervals to achieve a bioavailability which is equivalent to immediate release dosage forms administered in divided doses.

A known approach toward effecting the controlled release of orally administered drugs endeavors to achieve a zero order release profile whereby a substantially constant plasma level of the drug is maintained over a predetermined period of time. Although this known approach is suitable for many drugs, it is burdened with several significant disadvantages, and therefore is inappropriate particularly when used with first-pass metabolized drugs and others which are characterized by idiosyncratic pharmacokinetics or pharmacodynamics resulting in reduced bioavailability, altered drug-to-metabolite ratios, altered steady state levels of drug and metabolite, potential food-drug interactions, and altered pharmacodynamic response.

Strategies for reducing the dosing interval of orally administered drugs typically rely on changing the release pattern of the drug from a delivery system, or dosage form, such that the blood level profile of the drug falls within the therapeutic window of the dosing interval. Factoring into this strategy are the pharmacokinetics of the drug and the absorption rate of the drug in the gastrointestinal tract at the site of, and at the time when, the drug is released from the dosage form. The benefits of extended release delivery systems include a decrease in the frequency of dosing and a reduction in the variability of plasma levels of the administered drug over an immediate release dosage form.

In the case of drugs which do not exhibit first pass metabolism, the relationship between the extent of absorption and the bioavailability is linear. Accordingly, changes in bioavailability can be attributed to changes in the extent of absorption. However, in the case of drugs which exhibit first-pass metabolism, the relationship between extent of absorption (or input rate of drug into the portal system) and bioavailability is nonlinear, thereby leading to reduced bioavailability when drugs are administered at very low rates into the gastrointestinal tract.

There is therefore a need for a drug delivery system which yields a reduction in the oral dosing interval of drugs exhibiting first-pass metabolism while simultaneously maintaining bioavailability equivalent to the immediate release dosage form.

In conventional sustained release dosage forms, the bioavailability is compromised by the decreasing release rate. There is therefore a need for a drug dosage delivery system which will release fractions of the total dose at specified times and sites in the GI tract, and thereby minimize the effect of the release rate on the bioavailability.

Propranolol is a first-pass metabolized drug which exhibits non-linearity, or dose dependent bioavailability in the normal therapeutic dosage range. Propranolol hydrochloride, which is available commercially from Ayerst Laboratories, New York, N.Y. under the trademark INDERAL, was the first beta-adrenergic blocking agent to have widespread clinical usage in treating angina and hypertension. The biological half-life of propranolol in man is between two to six hours, and the dosage range is from about 40 to 2000 mg/day typically administered in two to four divided doses.

In order to extend the dosing interval, a controlled release form of propranolol was developed and sold by Ayerst Laboratories under the trademark INDERAL-LA. However, reports indicate that INDERAL-LA performs unsatisfactorily with respect to bioavailability. Although blood levels of propranolol are sustained for a period of 24 hours, the bioavailability is compromised by about 50% as compared to the immediate release dosage form administered in divided doses. It has been determined that such differences in bioavailability are caused by a higher degree of metabolism on first-pass through the liver for the lower release rate, and not incomplete absorption. Since patients on beta-adrenergic blockers are titrated to a particular dosage level given in divided doses, the benefit of once-a-day therapy is offset by possible changes in dosage needed to achieve efficacy.

It is evident from the foregoing that drugs which are eliminated by metabolism and exhibit a non-linear first-pass effect will have drug-to-metabolite level ratios which are dose rate dependent. Consequently, the kinetics of the parent compound and the metabolite are altered by dose rate leading to potentially different clinical responses to the drug. Propranolol, for example, has a bioavailability which varies from 20% to 80% due to dose rate differences. These differences were observed in humans where, for example, the bioavailability of a controlled release form of propranolol was 60% that of the immediate release dosage form, and the peak plasma levels were three-fold lower with the controlled release form leading to potential reduced clinical efficacy. As a result of these deficiencies, INDERAL-LA was required to be the subject of clinical studies to establish efficacy.

In addition to propranolol, other highly metabolized therapeutic agents are suitable for use with the drug dosage delivery system of the present invention. Some commercially available ones of such agents include other beta-adrenergic blockers such as metoprolol and timolol, calcium channel blockers such as verapamil, diltiazem and the anti-epileptic drug phenytoin. Given the large number of drugs which are eliminated by metabolism, there is a great need for an oral dosage form which reduces the relative extent of metabolism.

There are several significant goals which are desired to be realized with the use of a pulsed drug dosage delivery system which delivers doses of a drug at intervals timed to correspond to the administration of a plurality of immediate release doses at predetermined intervals. These include realization of: plasma level time curves equivalent to the immediate release dosage form; clinical efficacy, established through bioavailability, equivalent to the immediate release dosage form; increase in patient compliance as a result of a reduced or simplified dosing schedule; pharmacodynamic equivalence to that of the immediate release dosage form; metabolic rate equivalence to that obtained by conventional dosing schedules so that no unusual accumulation of metabolites or altered metabolic profile will result; accurate programmability of the pulse delay and determination of the fraction of the total dose at each pulse to achieve a variety of predeterminable dosing schedules and permit allowance for circadian rhythms to optimize plasma level time profiles throughout the day and night; and oral delivery of drugs which undergo particularly extensive first-pass metabolism (both gastro-intestinal and hepatic).

In order to accomplish these objectives with a controlled release dosage form, the dosage form must be reproducible, precise, and programmable. However, as a result of the complexity of developing such a system, there is not presently available a drug dosage delivery system of this type. In fact, at the present time, the operating principles of available controlled release dosage forms for oral delivery are based on relatively simple transport models which do not take into account many of the critical factors required to achieve reproducibility and precise programming, such as the physical properties of enteric coating films, including water diffusion into and plasticizer diffusion out of the polymeric coating films, and the consequent time dependent changes in the diffusion coefficient and permeability of the coating; and the time dependent mechanical properties of the coating and its polymer-plasticizer combination such as modulus of elasticity, tensile strength, type of failure (brittle, ductile, necking) or critical strain at failure. In addition, the composition of the core and the conditions under which the coatings are applied to the core can significantly alter the time rate of change of the properties of the coating. Such core variables as osmotic pressure inducing agents, viscosity inducing agents, disintegrants and the presence or absence of lipid materials can influence the swelling rate of the core and therefore the time for failure of the coating.

It is, therefore, an object of this invention to provide a drug delivery system for first-pass metabolized drugs, or other drugs wherein the relationship between extent of absorption and bioavailability is nonlinear, which drug delivery system will have bioavailability equivalent to the immediate release dosage form administered in divided doses.

It is another object of this invention to provide a drug delivery system which reduces oral dosing intervals for first-pass metabolized drugs, and hence improves patient compliance, while maintaining bioavailability equivalent to the immediate release dosage form administered in divided doses.

It is also an object of this invention to provide a drug delivery system for first-pass metabolized drugs which maintains higher plasma levels of drug, and reduces variability in the plasma levels, than currently available controlled release dosage forms.

It is a further object of this invention to provide a drug delivery system for first-pass metabolized drugs which will release an individual dose of drug at specified sites and time in the gastro-intestinal tract so that bioavailability will not be compromised by the decreased release rate of conventional controlled or sustained release dosage forms.

It is additionally an object of this invention to provide a drug delivery system which will provide pulse doses of drugs at precise and reproducible times which correspond to immediate release dosing intervals.

It is yet a further object of this invention to provide a drug delivery system which permits efficacious oral delivery of nonlinear first-pass drugs of the type which are extensively metabolized both gastro-intestinally and hepatically.

It is yet an additional object of this invention to provide a drug delivery system wherein the delivery rate into the portal system is increased, with a corresponding decrease in first pass metabolism.

It is also another object of this invention to provide a method for making a drug delivery device which reliably and precisely programs delivery of pulse doses of drug.

It is a yet further object of this invention to provide a drug delivery system which facilitates accommodation for circadian rhythms in order to optimize plasma level time profiles throughout the day and night.

It is still another object of this invention to provide a method of making a drug delivery system wherein optimal dosing schedules for two, or more drugs, can be achieved by tailoring pulse delivery of each drug to its individual pharmacokinetic and pharmacodynamic properties.

It is also a further object of this invention to provide a drug delivery system which yields a reduction in the oral dosing interval of drugs exhibiting first-pass metabolism while simultaneously maintaining bioavailability equivalent to the immediate release dosage form.

A still further object of this invention is to provide a drug delivery system for oral administration of a drug which reduces the relative extent of metabolism of the administered drug.

SUMMARY OF THE INVENTION

The foregoing and other objects are achieved by this invention which provides, in a system aspect thereof, a drug delivery system for administering a drug in controlled pulse doses in an aqueous environment in the body of a living being, over a predetermined dosage period of time. In accordance with this aspect of the invention, a unitary body, which is configured for administration to the body of the living being, contains a plurality of subunits. Each of the subunits has a core portion which contains an individual dose of the drug. The core is surrounded by a respectively associated coating portion which is formed of a selectable one of first and second polymer materials, in a specific embodiment of the invention. The coating portion is arranged to surround the core portion impermeably, with respect to the drug contained therein. Ones of the coating portions formed of the first polymer material are characterized by a respective predetermined period of core protection time which is different from that of the second polymer material. During the core protection time, release of the drug from its associated core portion is prevented after communication with the aqueous environment. Moreover, the period of core protection time is shorter than the predeterminable dosage time period.

In one embodiment of the invention, the first and second polymer materials are each formed of respective water-permeable polymers having respective tensile strengths and maximum elongations, such that the cohesive strength of the associated coating portions is exceeded after the respective predetermined periods of insolubility. In this manner, water which is obtained from the aqueous environment penetrates the coating portions and travels in an inward direction so as to create a pressurizing force in the core portion which causes the coating portion to rupture after expiration of the core protection time period. Thus, release of the drug to the aqueous environment is effected.

In a specific illustrative embodiment of the invention, the water-permeable polymer is cellulose acetate. Alternatively, the water-permeable polymer is selected from the group of water-permeable polymers consisting of cellulose acetate, ethyl acetate latexes, ethyl cellulose, cellulose butyrate, and Eudragit RS and Eudragit R 30 D (available from Rohm Pharma, W. Germany). In addition, there may be provided, in certain embodiments, a plasticizer, which is selected from the group of polyethylene glycol (PEG 200, PEG 1000), diethyl phthalate, and dibutyl phthalate.

In addition to a drug, or other therapeutic or diagnostic agent, viscosity enhancers, disintegrants, and other excipients may also be provided in the core portion.

In another specific embodiment of the invention, the aqueous environment has predetermined pH characteristics which cooperate with the coating portion which is provided with first and second polymer materials which are each pH-responsive. The pH-responsive polymer materials are soluble in the aqueous environment in response to the pH characteristic of the environment over a predetermined pH-responsive period of solubility to release drug to the environment. In such an embodiment, the pH-responsive material is selected from the group consisting of cellulose acetate phthalate, methyl cellulose phthalate, hydroxyethyl cellulose, cellulose acetate tetrahydrophthalate, cellulose acetate hexahydrophthalate, methyl-methacrylate, methacrylic acid and combinations thereof. Additionally, the pH-responsive material may be formed from a layered combination of cellulose acetate phthalate and a mixture of methyl-methacrylate and methylacrylic acid.

In the practice of the invention, the unitary body may be configured as a capsule, or as a tablet, and may contain illustratively ten subunits therein. Additionally, the drug to be administered may be a first-pass metabolized drug, which may, for example, be propranolol.

In accordance with a method aspect, the invention provides a method of producing a drug delivery device for administering a drug over a predetermined period of time to an aqueous region in the body of a living being. The method includes the steps of: forming first and second core units, each core unit containing a predetermined dosage of the drug; applying a first-type protective coating to the first core unit; and applying a second-type protective coating to the second core unit, the first-type and second-type protective coatings being formed of respective polymeric materials having different protective aspects from one another, whereby their respectively associated core units are exposed to the aqueous region after different periods of exposure thereto.

In accordance with a further method aspect, the invention provides a method of making a drug delivery device for administering drugs in a controlled dose at a time $T_p$ to an aqueous living body environment. This method aspect includes the steps of: forming a drug-containing core; coating the drug-containing core with a pH-sensitive polymeric material dissolved in a solvent, the pH-sensitive material being of the type which will dissolve in response to the pH of the aqueous living body environment, the pH-sensitive polymeric material comprising a weight percentage E of the solution; and curing the coating at a temperature T for a given time period, $T_p$ being described by the equation:

$$T_p = -36.9 + 0.113T + 1.27E - 0.00197(T*E),$$

where T is in K.

In a still further method aspect of the invention, a method of making a drug delivery device for administering drugs in a controlled dose at a time $T_p$ to an aqueous living body environment is provided with the steps of: forming a drug-containing core, the core containing a viscosity enhancing agent in concentration N; coating the drug-containing core with at least one polymeric material of the type which is water-permeable to permit water from the aqueous living body environment to penetrate the drug-containing core at a controlled rate in an inward direction, for creating a pressure which causes the coating to rupture at the predetermined release time, thereby releasing the drug to the aqueous environment at time $T_p$, the coating further containing a plasticizer in concentration P; and curing the coating at a temperature for a given time period, $T_p$ being described by the equation:

$$T_p = 8.3 + 0.064N - 0.312P + 0.0130(N*P).$$

BRIEF DESCRIPTION OF THE DRAWING

Comprehension of the invention is facilitated by reading the following detailed description, in conjunction with the annexed drawing, in which.

DETAILED DESCRIPTION

Figure 1:
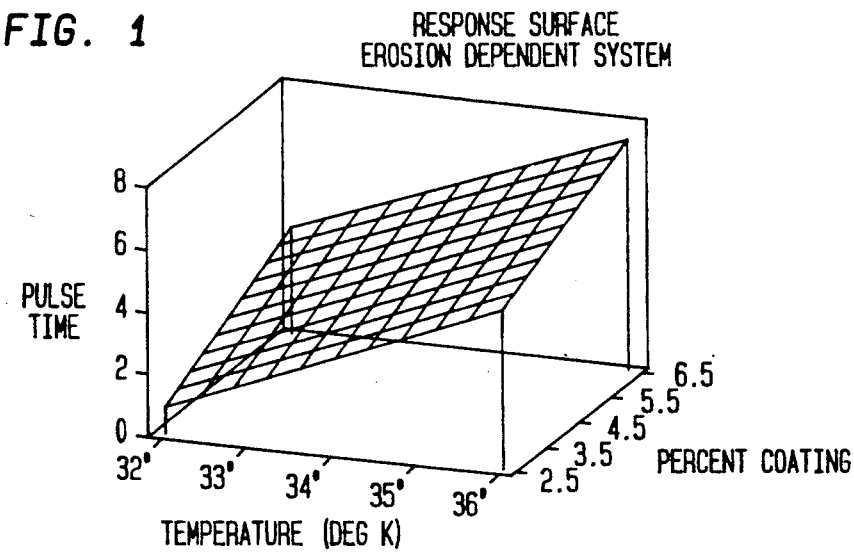
FIG. 1 is a response surface plot for a drug delivery system of the present invention of a pH-sensitive embodiment showing pulse time ($T_p$) as a function of percent enteric coating and curing temperature.

The drug delivery system, or dosage form, of the present invention has one or more, preferably less than 10, individual drug-containing units (also referred to herein as "subunits") in a unitary drug depot which dissolve at different sites and/or times in the gastrointestinal tract to release "pulse doses." The drug delivery system of the present invention is an extended interval dosage form as compared to a conventional sustained release dosage form which provides a slow, steady release of drug over a long period of time. The term pulse dose is used herein to describe the rapid delivery of a dose of drug ($F_1, F_2, \ldots, F_n$) at specific respective times ($T_1, T_2, \ldots, T_n$) into the portal system which is analogous to the rate of release from an immediate release dosage form administered according to an appropriate dosing schedule.

This drug delivery system has significant advantages for the oral administration of first-pass metabolized drugs which exhibit a non-linear relationship between input rate of the drug into the portal system and bioavailability. By devising a drug dosage delivery form which will release pulsed doses at rates comparable to immediate release forms, bioavailability will not be compromised by a decreased release rate as has been observed in conventional sustained release dosage forms for these drugs (e.g., INDERAL-LA).

The dissolution time of the individual subunits can be controlled by several methods to be discussed hereinbelow. Two illustrative means of controlling dissolution are (1) pH-sensitive enteric coatings which are eroded in response to the pH of the aqueous environment in the gastrointestinal tract and (2) permeability-controlled systems which are subject to disruption in response to absorption of water from the environment which creates a pressure as the core contents expand. Variation of process variables and coating and core compositions, in manners to be discussed hereinbelow, enables precise tailoring of the dissolution, or pulse, time of the individual unit cores. The individual units are combined into a unitary depot which may be single tablet or a gelatin capsule or any other form known in the art.

Illustratively, a two unit system may comprise an immediate release form (uncoated in some embodiments) and a polymeric coated form which would dissolve 6 to 12 hours later to provide a second dose of drug. A three unit system, for example, could provide an immediate release form, a 4–12 hour release form, and an 8–16 hour release form. The subunits may be combined into a single unitary body, such as a tablet or hard gelatin capsule, in any manner known in the art. Of course, these examples are only illustrative of the many specific embodiments which can be devised in accordance with the principles of the invention depending upon the desired dosing schedule of any particular drug.

Erosion-Dependent Systems

Enteric coatings of pH-sensitive polymers are employed to control the time of delivery of a drug-containing core composition to the small intestine of a living mammal.

Characteristics of suitable enteric coatings include: insolubility in the stomach, solubility in the intestines, no toxicity, moisture permeability resistance, stability, and good coating capability. A widely used enteric coating, and one which is used in the examples set forth herein, is cellulose acetate phthalate. Other well known cellulose ethers and ether derivatives including methylcellulose phthalate, hydroxyethylcellulose phthalate, cellulose acetate tetrahydrophthalate, and cellulose acetate hexahydrophthalate, are among the many polymeric materials which could be employed in the practice of the invention.

In illustrative embodiments, cellulose acetate phthalate (CAP) and/or methyl-methacrylate/methacrylic acid are suitable materials for the enteric coatings contemplated by the invention. These coatings delay release of the drug until the dosage form has passed from the stomach to the small intestine. In particular, the methyl-methacrylate/methacrylic acid coatings dissolve at a higher pH than CAP and are capable of extending the time of dissolution to four to eight hours in vitro in simulated intestinal fluid of pH 6.8. Methylmethacrylate is sold commercially by Rohm Pharma, W. Germany under the trademark Eudragit S100 and methacrylic acid is sold under the trademark Eudragit L100.

Although the core composition may comprise any drug, combination of drugs and therapeutic agents, including excipients and pharmacologically inert fillers as are known in the art, the invention is particularly suited to first-pass metabolized drugs which are not readily adaptable to conventional controlled release dosage forms. The examples herein are directed to the beta-adrenergic blocking agent propranolol as an exemplary first-pass metabolized drug. However, it is to be understood that any other drug or therapeutic/diagnostic agent can be formulated into the drug delivery system of the present invention. Moreover, more than one drug can be simultaneously administered in the dosage form of the present invention and each subunit, or pulse dose, can be tailored to compensate for the individual pharmacokinetics and pharmacodynamics of each.

Core Composition for Erosion-Dependent Embodiment

An illustrative core formulation for administration of propranolol is as follows:

| | |
|---|---|
| Propranolol HCl | 20 mg |
| Citric acid, anhydrous | 60 mg |
| Avicel pH 102 | 120 mg |
| AcDiSol | .12 mg |
| Lactose qs | 300 mg |

Avicel pH 102 (a form of microcrystalline cellulose distributed by FMC Corporation, Philadelphia, Pa.) and AcDiSol (FMC Corporation, Philadelphia, Pa) are disintegrants. Lactose is an inert filler which, in certain permeability-controlled embodiments, affects the osmotic pressure. All components will affect the pulse time ($T_p$). In this particular formulation, citric acid has been added for the purpose of creating a drastic pH change upon release of the core contents to facilitate tracking by a Heidelberg capsule in the in vivo studies.

In this particular embodiment, the unit cores were compressed on a Carver Press with a ⅜th inch die and deep-cut concave punches, at a pressure of 1600 psi for 60 seconds. Of course, other pressures and dwell times may be employed in the practice of the invention. Changes to the pressure and dwell time may affect the hardness and disintegration time of the unit core. An illustrative, and preferred, range for pressure is from about 500–3000 psi and for dwell time is from about 10–120 seconds. It is to be understood that any technique or device, conventional or otherwise, for producing compressed tablets may be employed in the fabrication of the individual unit cores and/or drug delivery system from a plurality of such unit cores. Another exemplary method is by use of a conventional rotary tablet press.

The unit cores are next coated with a solution of the desired coating polymer(s) in a solvent. The solvent may be organic, such as acetone, or in some embodiments, aqueous. Suitable machinery for coating include a rotating pan apparatus with a Sigma glass spray unit, a Uni-Glatt suspension coater or any other known fluidized bed equipment or pan coating technique typically used in the pharmaceutical industry. Next, the coated unit core is dried or cured for a predetermined time period at a predetermined temperature. The process variables, including spray rate, spray distance, atomization pressure, drying temperature and rate, and pan rotation speed, may effect the physical and mechanical properties of polymer coated drug cores.

Coating Formulations For Erosion-Dependent Embodiment

In an advantageous embodiment, the unit cores described hereinabove were pre-coated with a 3% film of CAP in order to reduce water permeability of a subsequently deposited coating of 5% Eudragit(s). This was necessary since the Eudragits were observed to immediately fail in simulated gastric fluid (pH 1.2).

Illustrative formulas for Eudragit and CAP coatings are as follows:

| Eudragit Coating Formula: | |
| --- | --- |
| Eudragit L100 | 3.0 g |
| Eudragit S100 | 3.0 g |
| Polyethylene Glycol | 1.5 g |
| Isopropyl Alcohol | 100 ml |
| Water | 2 ml |
| Talc | 1.2 g |
| CAP Coating Formula: | |
| Cellulose Acetate Phthalate | 5.4 g |
| Diethyl Phthalate | 1.4 g |
| Methylene Chloride | 50 ml |
| Methanol | 50 ml |

Varying the relative proportions of Eudragit L100 and Eudragit S100 in the formulation set forth above results in modification of release time. Table 1 summarizes the effect of varying Eudragit proportions on release time. All coating formulations were cured for 4 hours at 50° C. Release time, or pulse time $T_p$, for unit cores pre-coated with 3% CAP and 5% CAP, and then overcoated with Eudragit, are summarized therein.

TABLE 1

| Ratio of Eudragit (S100:L100) | $T_p$ (hours) |
| --- | --- |
| 50:50 | 2.5 |
| 70:30 | 3.0 |
| 85:15 | 2.1 + 0.1 (3%) |
| 85:15 | 2.7 + 0.3 (5%) |

The critical variables in the processing of the unit cores were identified as curing temperature (T) and percent Eudragit (E). A $2^2$ factorial design was conducted to ascertain the effects of these variables. Curing occurred over a four hour period.

| | LOW −1 | HIGH +1 |
| --- | --- | --- |
| T | 70° C. | 80° C. |
| E | 3% | 5% |

The effect of these variable and the main effect of each variable in terms of the pulse time ($T_p$) is given below in Table 2.

TABLE 2

| Experiment | T | E | T*E | $T_p$ Hours |
| --- | --- | --- | --- | --- |
| 1 | +1 | +1 | +1 | >24.0 |
| 2 | +1 | −1 | −1 | 5.3 + 0.7 |
| 3 | −1 | +1 | −1 | 4.9 + 0.5 |
| 4 | −1 | −1 | +1 | 3.0 + 0.1 |
| Main Effects* | 10.7 | 10.3 | 8.4 | |

*T = (24 + 5.3 − 4.9 − 3.0)/2 = 10.7
E = (24 − 5.3 + 4.9 − 3.0)/2 = 10.3
T*E = (24 − 5.3 − 4.9 + 3.0)/2 = 8.4

Table 2 demonstrates the optimization of $T_p$, or time of coating failure, in terms of the dependence of each of the named variables, as well as the interaction term (T*E). The temperature of curing (10.7) has the most significant effect. The equation which relates the variables to $T_p$ for the enteric coated unit cores described in the illustrative embodiment above is as follows:

$$T_p = -36.9 + 0.113T + 1.27E - 0.00197(T*E),$$

where the temperature is in °K.

A response surface plot relating the variables is shown in FIG. 1. Based on the response surface plot, a unit core was prepared containing 80 mg drug with a 5.6% Eudragit in acetone coating which was cured at 70° C. for four hours. In vitro testing in simulated intestinal fluid demonstrated a 5.7+0.1 hour pulse time (as compared to the 5.2 hours predicted by the equation).

In Vivo Testing of the Erosion-Dependent Embodiment

In vivo testing of the coated unit core, as described in the preceding paragraph, was accomplished by administering a coated unit core to four dogs along with an immediate release INDERAL tablet. Effectively, this resulted in the administration of a drug delivery system comprising two units, one immediate release (80 mg propranolol) and one pulse dose (80 mg propranolol timed for delivery approximately 5.7+0.1 hour).

A radiotelemetric device, the Heidelberg capsule (Telefunken Electro-Medical Devices, Inc., W. Germany) was also administered to the dogs for continuously monitoring pH of the environment during gastric emptying with respect to time. The radiotelemetric test procedure is described more completely in an article by Dressman and Amidon, Journal of Pharmaceutical Sciences, Vol. 73, No. 7, pages 935 to 938, July, 1984.

Figure 2:
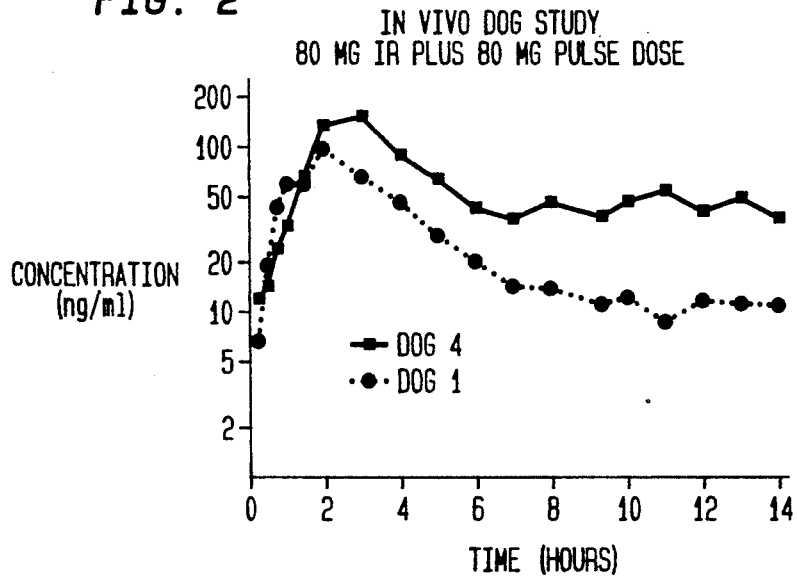
FIG. 2 is a graphical depiction of plasma level time curves for the oral administration of propranolol in a drug delivery system of the present invention for two dogs.

Of the four dogs, two dogs did not empty the Heidelberg capsule in the first eight hours and the experiment with respect to these two dogs was canceled. With respect to the remaining two dogs, gastric emptying occurred at 1.6 and 2.0 hours, respectively. Plasma levels of free propranolol were measured over a period of 14 hours. FIG. 2 shows the plasma level time curves for the two dogs. The plasma levels were maintained at controlled levels starting seven to eight hours into the study (5-6 hours after gastric emptying) indicating the release of the pulse dose.

One disadvantage of the pH-dependent system is that release of the drug in vivo is affected by the variable pH in the small intestine. Moreover, release time is affected by gastric emptying. Therefore, a second approach which is pH independent is set forth in detail hereinbelow. However, as the results shown hereinabove indicate, pulse time can be controlled by careful choice of core composition, coating composition, and coating curing process variables.

Permeability-Controlled Systems

Permeability-controlled systems are generally based on polymeric coatings which are water-permeable to permit water from the aqueous environment in the gastrointestinal tract of a living being to enter into a coated drug-containing core at a controllable rate and to displace air from the core followed by a build-up of pressure as the core contents expand until the coating is ruptured at the appropriate time.

In one embodiment of the invention, a lipid material, such as mineral oil, is incorporated in the core composition. The polymeric coating is chosen to allow selectively the lipid to diffuse out of the core as water diffuses into the core. The advantage of this formulation is that the core will maintain a constant weight because a constant internal pressure is exerted on the coating film during the time when the lipid material is being displaced. After all of the lipid material has been depleted from the core, the internal pressure in the core will increase until the critical stress has been reached and the coating ruptures.

The polymeric coating for the permeability-controlled system must be impermeable to the drug and permeable to the intake of water and the expulsion of air. The core composition for permeability-controlled systems may advantageously contain osmotic agents, such as salt, to facilitate water transport to the core.

The following are lists of variables which must be taken into consideration in the successful design of a permeability-controlled drug delivery system of the present invention.

Formulation Variables For Permeability-Controlled Embodiments (1) The type and amount of osmotic agent included in the core and its influence on the hydraulic permeability ($L_p$) of water through the coating film. Suitable osmotic agents include sodium chloride, potassium chloride and various sugars such as lactose, sucrose, mannitol, fructose, sorbitol.

(2) The type and amount of low bulk density solid and/or displaceable lipid material and their effects on coating film failure time. Agents to increase the displaceable volume in the tablets include fumed silica dioxide and lipids, such as mineral oil.

(3) The choice of viscosity enhancers, disintegrants, and other excipients in the core formulation. Viscosity enhancers include sodium carboxymethyl cellulose (NaCMC, low and high viscosity), alginic acid (low and high viscosity), polycarbophil, and fumed silica. Exemplary disintegrants include AcDiSol, Avicel, and Explotab (available from Edward Mendell Co., Inc., Carmel, N.Y.). Other excipients or fillers of any type known or used in the art may be included.

(4) The choice of polymer and plasticizer as well as their initial and final concentration in the polymer coat. Representative polymers include cellulose acetate, ethyl acetate latexes, ethyl cellulose and cellulose butyrate and Eudragit RS and Eudragit E 30 D. Although some of these polymers are soluble in organic solvents and applied in a weight percentage of organic solvent, such as acetone, others are water-based. Plasticizers include PEG 200, PEG 1000, diethyl phthalate and dibutyl phthalate, typically in concentrations of 0 to 20%.

Process Variables

In addition to the formulation of the core and coating material(s), process variables may affect the physical and mechanical properties of polymer coated cores. The process variables for the coating include spray rate, spray distance, atomization pressure, drying temperature and rate, and pan rotation speed. Process variables for the core may be controlled by the determination of the hardness and disintegration time for the core.

Core Composition for Permeability-Controlled Embodiment

In a specific illustrative embodiment of the invention, the following core composition was utilized:

| | |
|---|---|
| NaCl | 100.0 mg |
| Avicel pH 102 | 100.0 mg |
| NaCMC (High Viscosity) | 25.0 mg |
| AcDiSol | 20.0 mg |
| Phenol Red | 0.5 mg |
| Propranolol HCl | 2.0 mg |
| Oil Soluble Dye | 0.25 mg |
| Lactose qs | 500.0 mg |

NaCl acts as an osmotic agent, sodium carboxymethyl cellulose (NaCMC) is a viscosity enhancer, and the remaining ingredients are fillers and disintegrants. Unit cores were compressed on a Carver Press with a ⅜th inch die and deep-cut concave punches at a pressure of 2000 psi for 30 seconds.

Coating Composition For Permeability-Controlled Embodiment

The unit cores were coated with a 2% wt./wt. solution of cellulose acetate in acetone of the formula shown below. The coating was applied with a Sigma glass spray unit.

In a specific illustrative embodiment, the permeable polymeric coating is cellulose acetate (CA-398-10 available from FMC Corporation, Philadelphia, Pa.) and a plasticizer (PEG 200, a polyethylene glycol available from Sigma Chemical Co., St. Louis, Mo.):

| | |
|---|---|
| Cellulose Acetate CA-398-10 | 3.5 g |
| PEG 200 | 0.7 g (20% of CA-398-10) |
| Acetone | 100. ml |

The physical and mechanical properties of the water permeable coating will change with time in the presence of water in the gastrointestinal tract because water diffuses into and plasticizer diffuses out of the film. In an illustrative embodiment, these effects have been evaluated for cellulose acetate films. The isochronal modulus of cellulose acetate films which had been soaked in a phosphate buffer of pH 6.8 for periods of 2 and 7.5 hours was measured on a Mettler TMA-40 Thermo-Mechanical Analyzer for 7 seconds at 37° C. The results are given below in Table 3 for cellulose acetate films including a plasticizer (20% PEG 200) in the formulation and without a plasticizer.

TABLE 3

| | Isochronal Modulus (Kpsi) | |
|---|---|---|
| Time of Buffer Pre-Treatment (hours) | Without Plasticizer | With Plasticizer |
| 0 | 369.9 | 220.2 |
| 2.0 | 278.2 | 204.4 |

TABLE 3-continued

| Time of Buffer Pre-Treatment (hours) | Isochronal Modulus (Kpsi) | |
|---|---|---|
| | Without Plasticizer | With Plasticizer |
| 7.5 | 275.8 | 202.9 |

While the cellulose acetate film is viscoelastic as evidenced by a modulus change with time, there is a 30% decrease in modulus after two hours of soaking in buffer. The inclusion of a plasticizer not only lowers the isochronal modulus, thereby producing a more compliant film, but lowers the change in modulus (approximately 10% versus 30%) with soaking.

The critical variables were identified as the concentrations of NaCMC and AcDiSol in the core formulation and the concentration of PEG 200 relative to cellulose acetate in the coating formula. A full $2^3$ factorial design was run with the following critical variables:

| | LOW −1 | HIGH +1 |
|---|---|---|
| N = Na CMC | 0% | 10% |
| A = AcDiSoL | 0% | 8% |
| P = PEG 200 | 0% | 40% |

The effect of these variables and the main effect of each of the variables in terms of the pulse time are given in Table 4:

TABLE 4

| Experiment | N | A | P | $T_p$ Hours |
|---|---|---|---|---|
| 1 | +1 | +1 | +1 | 2.0 |
| 2 | +1 | +1 | −1 | 9.5 |
| 3 | +1 | −1 | +1 | 1.5 |
| 4 | +1 | −1 | −1 | 9.0 |
| 5 | −1 | +1 | +1 | >24.0 |
| 6 | −1 | +1 | −1 | >24.0 |
| 7 | −1 | −1 | +1 | >24.0 |
| 8 | −1 | −1 | −1 | >24.0 |
| 9 | 0 | 0 | 0 | 4.0 |
| Main Effects | −19.5 | 0.06 | −3.75 | |

Table 4 demonstrates that the effect of NaCMC and the percentage of PEG 200 in the coating solution will affect the pulse time. In particular, NaCMC concentration in the core will have a large effect which lowers the pulse time (−19.5). However, there is relatively little dependence on AcDiSol concentration (0.6). Therefore a $2^2$ factorial design was run with the following variables:

| | LOW −1 | HIGH +1 |
|---|---|---|
| N = Na CMC | 5% | 10% |
| P = PEG 200 | 5% | 10% |

The result of this factorial design with respect to pulse time is shown in Table 5:

TABLE 5

| Experiment | N | P | N*P | $T_p$ Hours |
|---|---|---|---|---|
| 1 | +1 | +1 | +1 | 6.8 + 0.1 |
| 2 | +1 | −1 | −1 | 7.0 + 0.2 |
| 3 | −1 | +1 | −1 | 6.8 + 0.1 |
| 4 | −1 | −1 | +1 | 6.3 + 0.3 |
| 5 | 0 | 0 | 0 | 6.3 + 0.3 |
| Main Effects | −0.4 | 0.6 | 0.4 | |

Reference to the $T_p$ column confirms that the pulse time can be reproducibly delayed. For example, the center point in the above design (7.5% NaCMC and 7.5% PEG 200) gave a 6.3 hour pulse time with a standard error of 0.3 hours. The pulse time for the permeability-controlled embodiment hereinabove described can be expressed in terms of the dependence of each of the variable as well as the interaction term (N*P):

$$T_p = 8.13 + 0.0645N - 0.312P + 0.0130(N*P)$$

Figure 3:
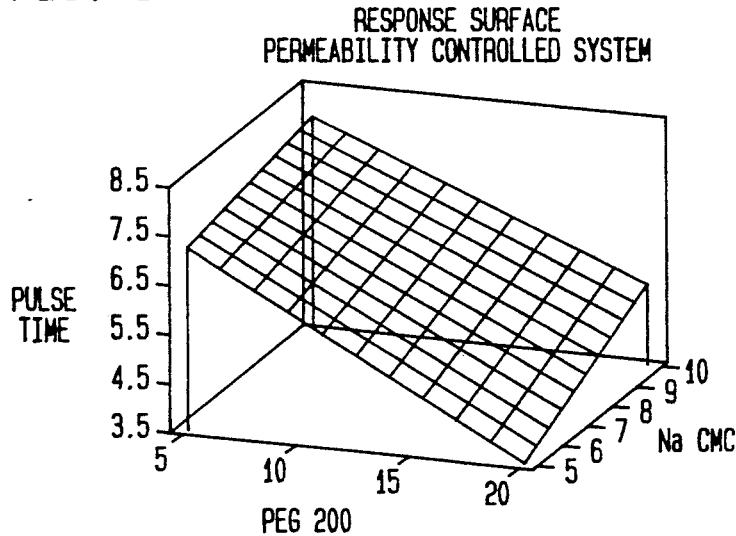
FIG. 3 is a response surface plot for a permeability-controlled embodiment of a drug delivery system of the present invention showing pulse time ($T_p$) as a function of percent viscosity enhancer (NaCMC) in a drug-containing core and percent plasticizer (PEG 200) in a coating formulation.
Figure 4:
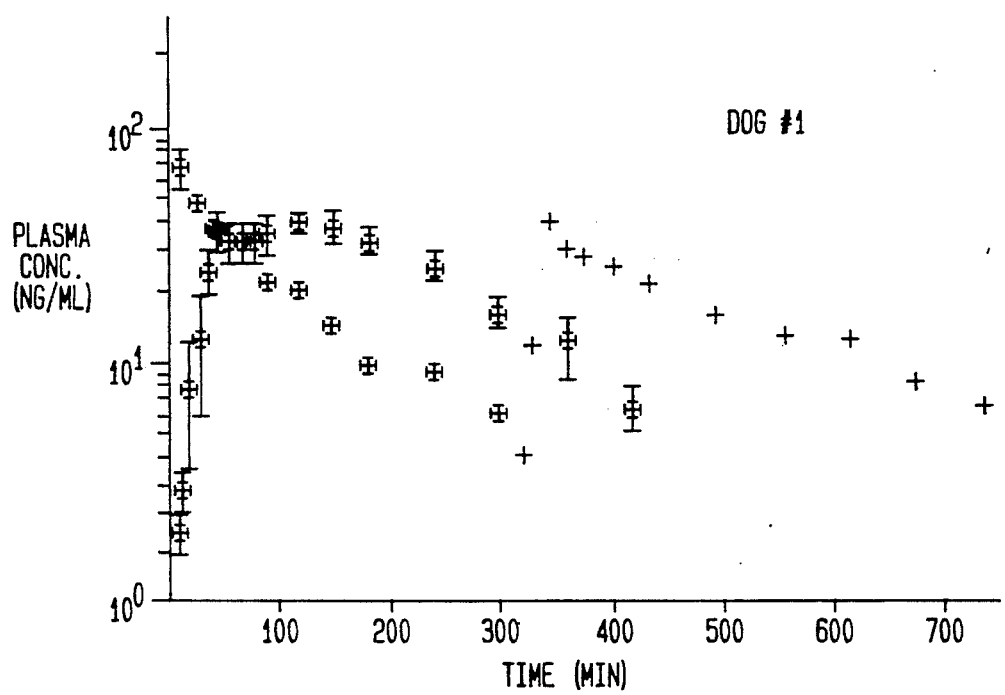
FIGS. 4, 5, 6 and 7 are graphical plots of plasma level time curves for respective individual dogs representing the amount of free propranolol in blood specimens (ng/ml) over time (minutes) following administration of propranolol by IV and orally in an immediate release form (INDERAL 80mg) and a permeability-controlled drug delivery system embodiment of the present invention.
Figure 8:
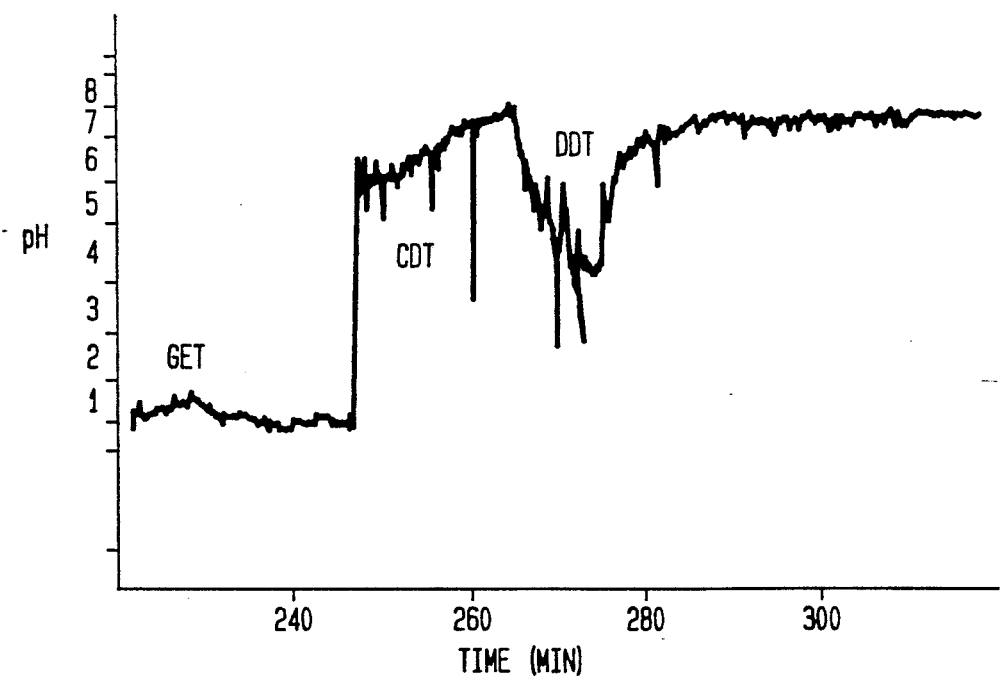
FIGS. 8, 9, 10 and 11 are tracings of the pH-time profile in the gastrointestinal tract of the respective individual dogs (FIGS. 4 to 7) after administration of the permeability-controlled drug delivery system of the present invention.
Figure 5:
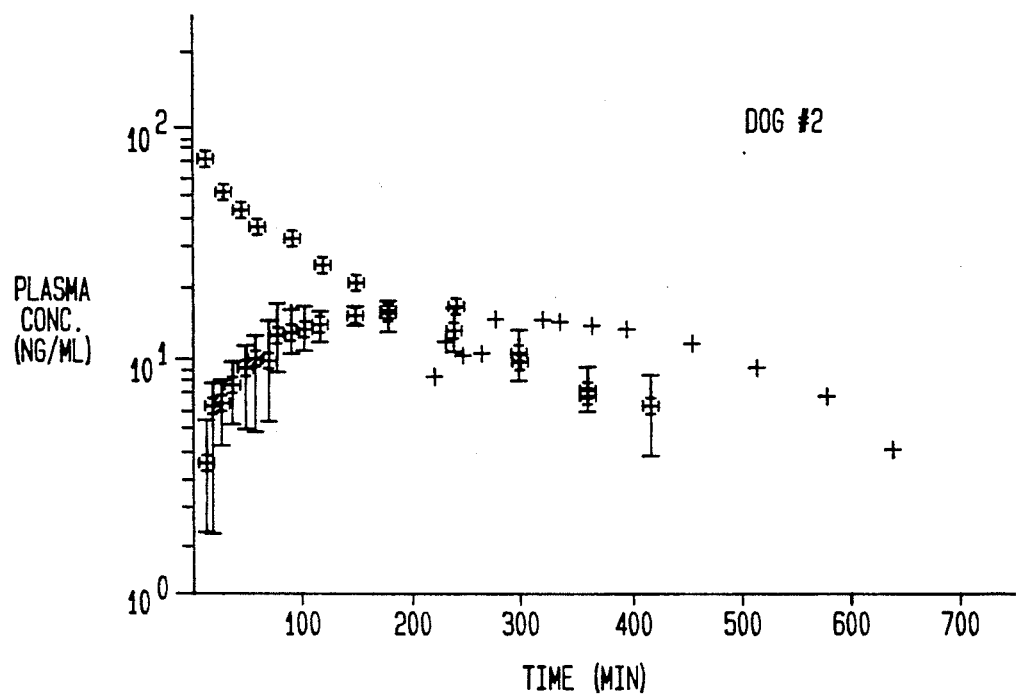
Figure 9:
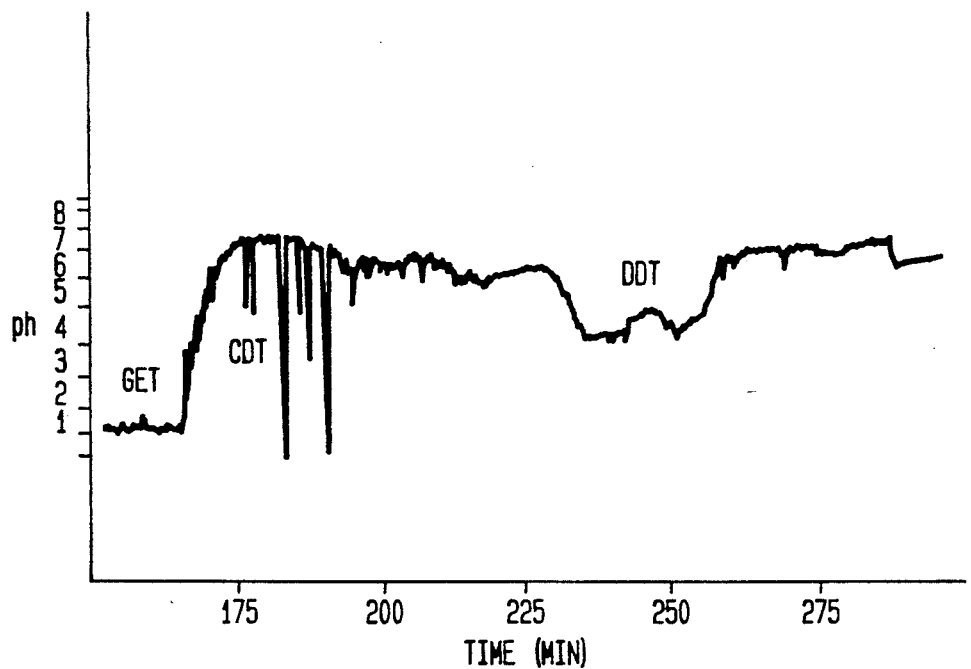
Figure 6:
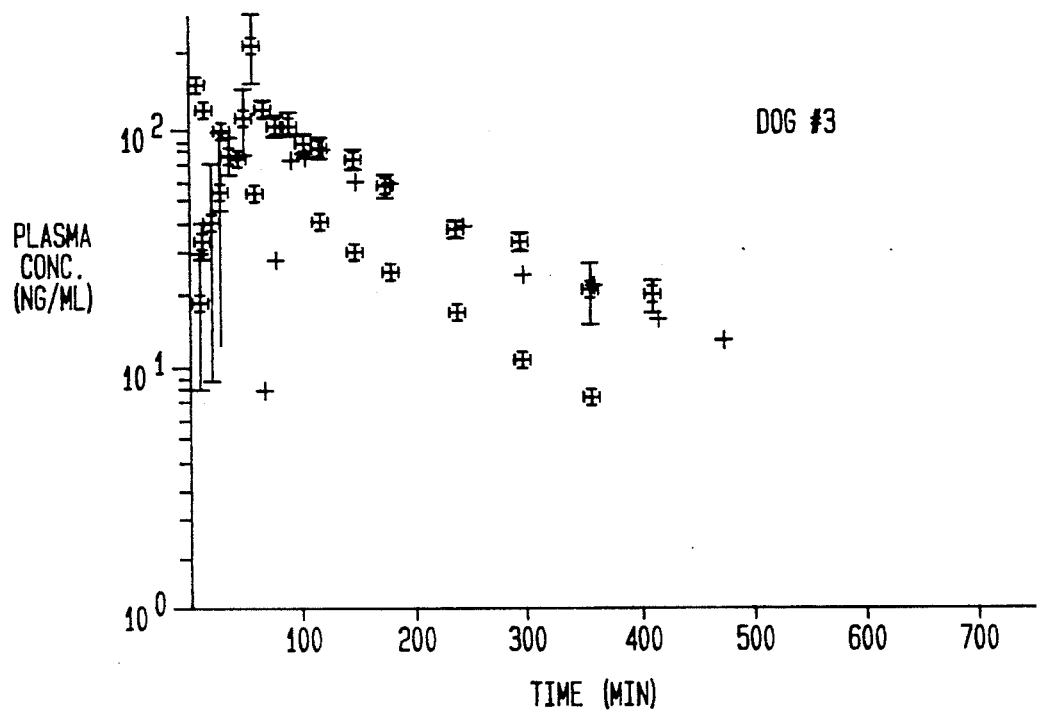
Figure 10:
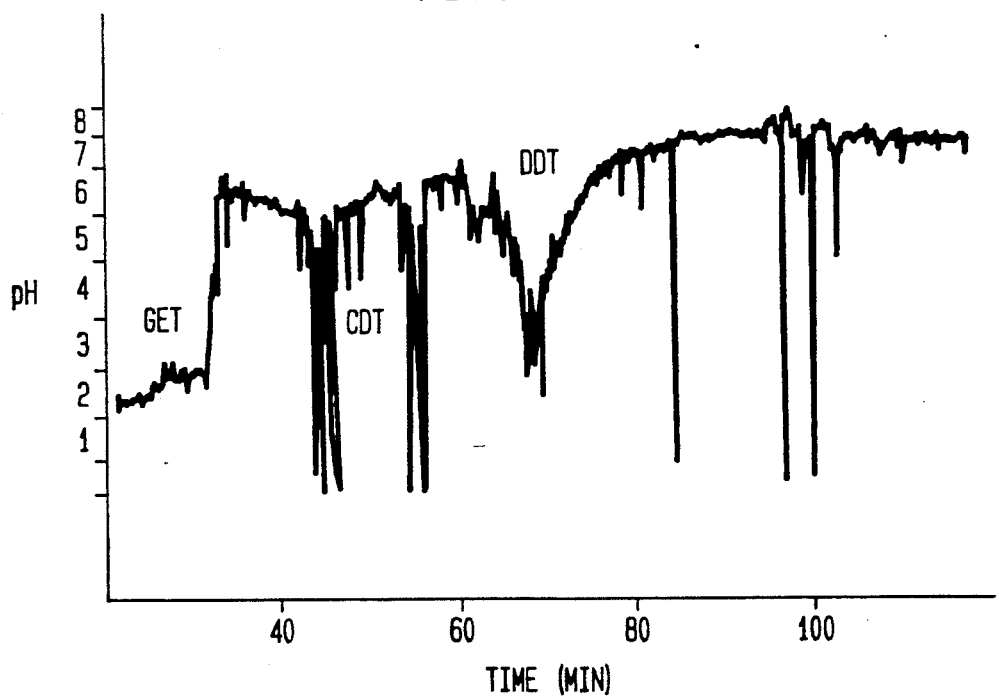
Figure 7:
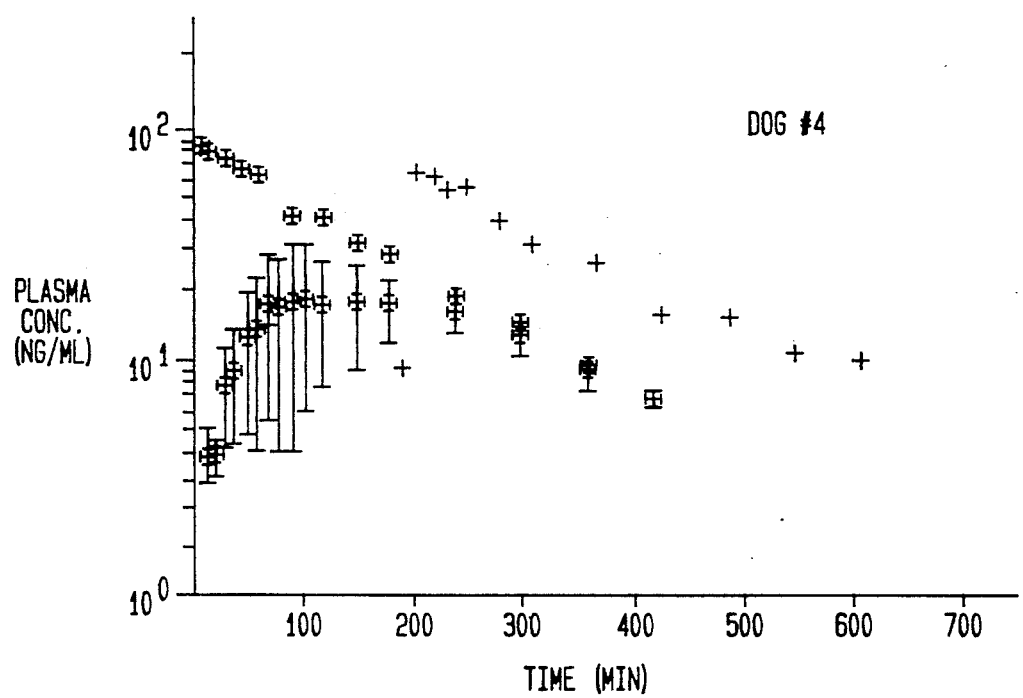
Figure 11:
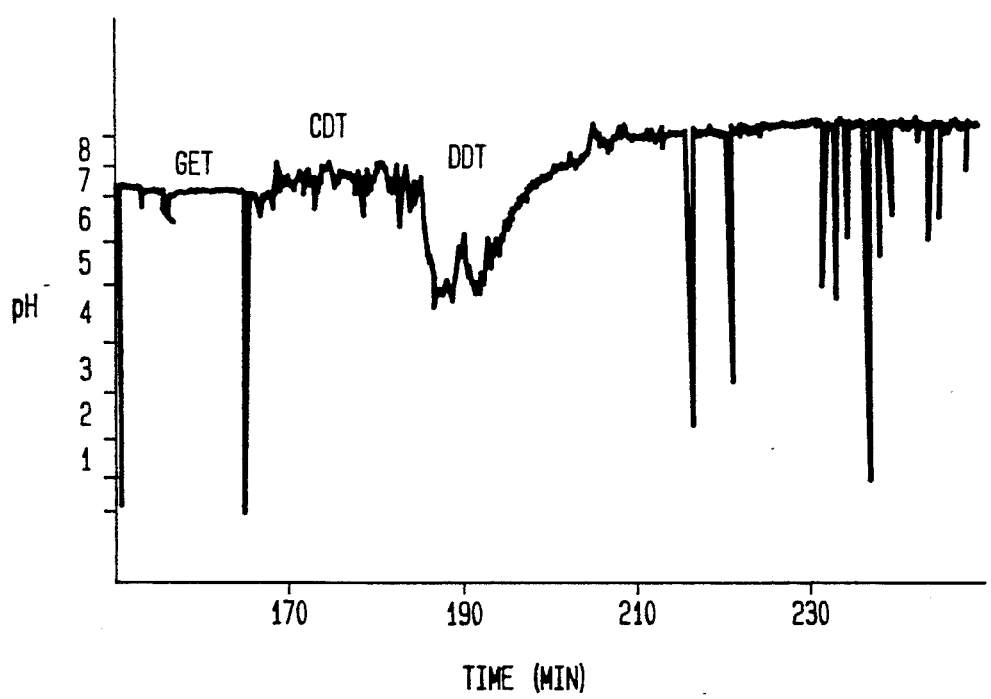

A response surface plot relating these variables is shown in FIG. 3. Pulse time for individual unit cores can be varied in accordance with the desired dosing schedule by modifying the NaCMC concentration in the core composition and the plasticizer content of the CAP coating in accordance with the response surface plot.

Additional Examples of Coatings and Core Compositions for Permeability-Controlled Embodiments For the purposes of illustration, Table 6 gives ten enteric coating formulas containing a mixture of the polymers cellulose acetate (CA 398-10) and cellulose acetate butyrate (CAB 171-15S, available from FMC Corporation, Philadelphia, Pa.) in a 3.5% wt./wt. solution in acetone. The plasticizer, polyethylene glycol (PEG 200), is expressed as a percentage relative to the polymer concentration.

In preparing solutions containing 80% cellulose acetate butyrate (CAB 171-15S) and PEG 200 were dissolved in acetone and filtered through filter paper. The volume of acetone was restored to 100 ml before cellulose acetate (CA 398-10) was added.

TABLE 6

| | COATING FORMULAS COMPONENTS | | |
|---|---|---|---|
| Formula No. | CA 398-10 | CAB 171-15S | PEG 200 |
| 1 | 40 | 60 | 20 |
| 2 | 40 | 60 | 40 |
| 3 | 60 | 40 | 15 |
| 4 | 60 | 40 | 20 |
| 5 | 60 | 40 | 40 |
| 6 | 20 | 80 | 20 |
| 7 | 20 | 80 | 40 |
| 8 | 20 | 80 | 60 |
| 9 | 02 | 80 | 80 |
| 10 | 20 | 80 | 100 |

Unit cores were prepared by combining the identified ingredients and mixing well. A few milligrams of Sudan III or Sudan Orange G dye were added as a aid in the in vitro studies for identifying when the coated tablets dissolve and release contents. The combined ingredients were dried in a 50° C. oven for 4 hours. Portions weighing 500 mg were compressed at 2000 psi for 30 seconds using a Carver laboratory press.

The unit core tables were weighed and then coated in a rotating pan using a Sigma glass sprayer. During spraying, a stream of air was applied to aid drying and prevent sticking. After coating, the tablets were dried in a 50° C. oven for 4 hours. The coated cores, or tablets, were weighed and the weight percent of coating was determined.

The tablet were tested in 15 ml of a 0.85% w/v NaCl solution to determine water uptake. Water uptake was determined by reweighing the tablets at predetermined intervals, specifically 0.5 hours after immersion and hourly thereafter. The time of release, or rupture, was visually observed when the dye contained in the core formulation colored the NaCl solution. The time of release ($T_p$) for various core and coating combinations, are given below in Tables 7-10. Referring to the Tables, the "Coating %" refers to coating as a percent of total weight of the tablet and the term "Coating #" refers to the formulation numbers from Table 6. The quantities of the core components are given in mg.

Tables 7-10 confirm that variation in the core formulation and coating composition can vary the pulse time from 1 to 24 hours. Curing process parameters were not varied. With this wide range of pulse times, drug delivery systems can be constructed to deliver drugs dosed every 4 to 6 hours, for example, in a once a day dosage form.

TABLE 7

SUMMARY OF COATINGS AND CORES TESTED

| CORE FORMULA | A | B | C | D | E |
|---|---|---|---|---|---|
| NACL | 20 | 20 | 20 | 20 | 20 |
| AVICEL | 20 | 20 | 20 | 20 | 40 |
| CMC | 10 | 5 | 5 | 5 | 5 |
| LACTOSE | 50 | 51 | 47 | 47.5 | 31 |
| ACDISOL | 0 | 4 | 8 | 0 | 4 |
| SILICA | 0 | 0 | 0 | 7.5 | 0 |
| COATING % | 2.4 | 1.5 | 1.5 | 2.5 | 2.5 |
| Coating # | 1 | 1 | 1 | 2 | 2 |
| RELEASE (HR) | >24 | 11.5 | >24 | 6.5 | 6.5 |

TABLE 8

SUMMARY OF COATINGS AND CORES TESTED

| CORE FORMULA | A-1 | B-1 | C-1 | D-1 | E-1 | F-1 | G-1 | H-1 | I-1 |
|---|---|---|---|---|---|---|---|---|---|
| NACL | 20 | 20 | 20 | 20 | 20 | 20 | 0 | 0 | 0 |
| AVICEL | 20 | 20 | 20 | 20 | 20 | 40 | 20 | 20 | 20 |
| CMC | 2 | 5 | 5 | 5 | 5 | 5 | 2 | 1 | 2 |
| LACTOSE | 54 | 51 | 47 | 47.5 | 47.5 | 31 | 54 | 60 | 64 |
| ACDISOL | 4 | 4 | 8 | 0 | 0 | 4 | 4 | 4 | 4 |
| SILICA | 0 | 0 | 0 | 7.5 | 7.5 | 0 | 0 | 0 | 0 |
| SORBITOL | 0 | 0 | 0 | 0 | 0 | 0 | 20 | 15 | 10 |
| COATING % | 1.5 | 1.5 | 1.5 | 1.96 | 2.5 | 2.5 | 2.1 | 2.1 | 2.4 |
| Coating # | 4 | 4 | 4 | 4 | 5 | 5 | 5 | 5 | 5 |
| RELEASE (HR) | >24 | >24 | >24 | 12.5 | 6 | 2.2 | 12.3 | 10 | 9 |

TABLE 9

SUMMARY OF COATINGS AND CORES TESTED

| CORE FORMULA | A-2 | B-2 | C-2 | D-2 | E-2 | F-2 | H-2* | I-2* | J-2 |
|---|---|---|---|---|---|---|---|---|---|
| NACL | 20 | 20 | 20 | 20 | 20 | 0 | 0 | 0 | 20 |
| AVICEL | 40 | 40 | 40 | 40 | 40 | 20 | 20 | 20 | 40 |
| CMC | 2 | 0 | 2 | 2 | 2 | 2 | 2 | 2 | 2 |
| LACTOSE | 24 | 26 | 24 | 24 | 24 | 54 | 54 | 54 | 24 |
| ACDISOL | 4 | 4 | 4 | 4 | 4 | 4 | 4 | 4 | 4 |
| SORBITOL | 10 | 10 | 10 | 10 | 10 | 20 | 20 | 20 | 10 |
| COATING % | 0.7 | 0.7 | 1.1 | 1.1 | 2.6 | 2.2 | 1.1 | 2.9 | 1.7 |
| Coating # | 6 | 6 | 7 | 8 | 8 | 8 | 8 | 8 | 9 |
| RELEASE (HR) | 1 | 0.5 | 3.5 | 0.5 | 4 | 9 | 0.5 | 1.7 | 1 |

*1.2% talc added

TABLE 10

SUMMARY OF COATINGS AND CORES TESTED

| CORE FORMULA | A-3 | B-3 | C-3 | D-3 | E-3 | F-3 | H-3 | I-3 | J-3 |
|---|---|---|---|---|---|---|---|---|---|
| NACL | 20 | 20 | 20 | 20 | 20 | 0 | 0 | 0 | 0 |
| AVICEL | 40 | 30 | 30 | 20 | 20 | 20 | 20 | 20 | 20 |
| CMC | 2 | 5 | 5 | 2 | 2 | 2 | 2 | 2 | 2 |
| LACTOSE | 24 | 41 | 41 | 54 | 50 | 54 | 54 | 54 | 54 |
| ACDISOL | 4 | 4 | 4 | 4 | 8 | 4 | 4 | 4 | 4 |
| SORBITOL | 10 | 0 | 0 | 0 | 0 | 20 | 20 | 20 | 20 |
| COATING % | 2.8 | 1.7 | 2.8 | 1.7 | 1.7 | 1.7 | 2.8 | 2.8 | 2.2 |
| Coating # | 9 | 9 | 9 | 9 | 9 | 9 | 9 | 10 | 8 |
| RELEASE (HR) | 1 | <0.5 | 0.5 | <0.5 | <0.5 | 1 | 3 | 0.5 | 9 |

Tables 11, 13, 15, and 17 give additional exemplary formulas for unit cores. The unit cores are prepared and coated with coating formulation #5 from Table 6 in accordance with the method described hereinabove. In the specific examples given below, the coating weight, as a percent of the total tablet weight after drying, is varied. Tables 12, 14, 16, and 18 show the results of visual observance of coating failure and percent of the sample which split and release contents at specific intervals. In some cases, the coating has been observed to split, particularly at the tablet edges, but the core contents do not release.

TABLE 11

COATING #5 - Table 6
% COATING: 1.2% total tablet weight

| FORMULA | A | B | C | D | E | F | G | H | I |
|---|---|---|---|---|---|---|---|---|---|
| SORBITOL | 20% | 20% | 20% | 20% | 10% | 10% | 10% | 10% | 15% |
| NaCl | 20% | 20% | 0% | 0% | 20% | 20% | 0% | 0% | 10% |
| AVICEL | 40% | 20% | 40% | 20% | 40% | 20% | 40% | 20% | 30% |
| CMC | 2% | 2% | 2% | 2% | 2% | 2% | 2% | 2% | 2% |
| ACDISOL | 4% | 4% | 4% | 4% | 4% | 4% | 4% | 4% | 4% |
| LACTOSE | 14% | 34% | 34% | 54% | 24% | 44% | 44% | 64% | 39% |
| TOTALS | 100% | 100% | 100% | 100% | 100% | 100% | 100% | 100% | 100% |

TABLE 12

COATING #5 - Table 6
% COATING: 1.2% total tablet weight

| FORMULA (TABLE 11) | COATING FAILURE (hrs) | % SPLITTING @ 30 (minutes) | % SPLITTING @ 60 (minutes) | % RELEASE @ 60 (minutes) | % RELEASE @ 120 (minutes) |
|---|---|---|---|---|---|
| A | >24.00 | 0.00 | 0.00 | 0.00 | 0.00 |
| B | 16.42 | 0.67 | 0.67 | 0.67 | 0.67 |
| C | 3.08 | 53.33 | 60.00 | 5.00 | 16.67 |
| D | 3.33 | 11.67 | 15.00 | 2.00 | 2.00 |
| E | 16.67 | 16.67 | 25.00 | 16.67 | 25.00 |
| F | 16.17 | 8.33 | 8.33 | 0.67 | 1.67 |
| G | 3.67 | 32.00 | 32.00 | 5.33 | 10.33 |
| H | 1.92 | 36.67 | 36.67 | 4.00 | 4.00 |
| I | 8.50 | 15.00 | 20.00 | 2.33 | 4.00 |
| AVE. | 10.4 | 19.4 | 22.0 | 4.1 | 7.1 |

TABLE 13

COATING #5 - Table 6
% COATING: 1.1% total tablet weight

| FORMULA | A-1 | B-1 | C-1 | D-1 | E-1 | F-1 | G-1 | H-1 | I-1 |
|---|---|---|---|---|---|---|---|---|---|
| SORBITOL | 20% | 20% | 20% | 20% | 10% | 10% | 10% | 10% | 15% |
| NaCl | 4% | 4% | 0% | 0% | 4% | 4% | 0% | 0% | 2% |
| AVICEL | 60% | 30% | 60% | 30% | 60% | 30% | 60% | 30% | 45% |
| CMC | 2% | 2% | 2% | 2% | 2% | 2% | 2% | 2% | 2% |
| ACDISOL | 4% | 4% | 4% | 4% | 4% | 4% | 4% | 4% | 4% |
| LACTOSE | 10% | 40% | 14% | 44% | 20% | 50% | 24% | 54% | 32% |
| TOTALS | 100% | 100% | 100% | 100% | 100% | 100% | 100% | 100% | 100% |

TABLE 14

COATING #5 - Table 6
% COATING: 1.1% total tablet weight

| FORMULA (TABLE 13) | COATING FAILURE (hrs) | % SPLITTING @ 30 (minutes) | % SPLITTING @ 60 (minutes) | % RELEASE @ 60 (minutes) | % RELEASE @ 120 (minutes) |
|---|---|---|---|---|---|
| A-1 | 0.45 | 80.00 | 93.30 | 63.30 | 81.70 |
| B-1 | >24.00 | 0.00 | 0.00 | 0.00 | 0.00 |
| C-1 | 0.52 | 85.00 | 90.00 | 48.30 | 65.00 |
| D-1 | 2.20 | 50.00 | 51.70 | 8.30 | 13.30 |
| E-1 | 0.34 | 76.70 | 83.30 | 50.00 | 80.00 |
| F-1 | >24.00 | 0.00 | 0.00 | 0.00 | 0.00 |
| G-1 | 0.80 | 80.00 | 88.30 | 50.00 | 55.00 |
| H-1 | 1.40 | 40.00 | 46.70 | 2.70 | 0.00 |
| I-1 | >24.00 | 0.00 | 0.00 | 0.00 | 0.00 |
| AVE. | 8.60 | 45.7 | 50.4 | 24.7 | 32.8 |

TABLE 15

COATING #5 - Table 6
% COATING: 1.9% total tablet weight

| FORMULA | A-2 | B-2 | C-2 | D-2 | E-2 | F-2 | G-2 | H-2 | I-2 |
|---|---|---|---|---|---|---|---|---|---|
| SORBITOL | 20% | 20% | 20% | 20% | 10% | 10% | 10% | 10% | 15% |
| NaCl | 4% | 4% | 0% | 0% | 4% | 4% | 0% | 0% | 2% |
| AVICEL | 60% | 30% | 60% | 30% | 60% | 30% | 60% | 30% | 45% |
| CMC | 2% | 2% | 2% | 2% | 2% | 2% | 2% | 2% | 2% |
| ACDISOL | 4% | 4% | 4% | 4% | 4% | 4% | 4% | 4% | 4% |
| LACTOSE | 10% | 40% | 14% | 44% | 20% | 50% | 24% | 54% | 32% |
| TOTALS | 100% | 100% | 100% | 100% | 100% | 100% | 100% | 100% | 100% |

TABLE 16

COATING #5 - Table 6
% COATING: 1.9% total tablet weight

| FORMULA (TABLE 15) | COATING FAILURE (hrs) | % SPLITTING @ 30 (minutes) | % SPLITTING @ 60 (minutes) | % RELEASE @ 60 (minutes) | % RELEASE @ 120 (minutes) |
|---|---|---|---|---|---|
| A-2 | >24.00 | 0.00 | 0.00 | 0.00 | 0.00 |
| B-2 | >24.00 | 0.00 | 0.00 | 0.00 | 0.00 |
| C-2 | 1.50 | 83.30 | 90.00 | 50.00 | 65.00 |
| D-2 | 5.10 | 15.00 | 17.50 | 2.00 | 2.00 |
| E-2 | 0.95 | 75.00 | 85.00 | 60.00 | 72.50 |
| F-2 | >24.00 | 0.00 | 0.00 | 0.00 | 0.00 |
| G-2 | 5.60 | 67.50 | 75.00 | 22.50 | 30.00 |
| H-2 | >24.00 | 0.00 | 0.00 | 0.00 | 0.00 |
| I-2 | >24.00 | 0.00 | 0.00 | 0.00 | 0.00 |
| AVE. | 14.8 | 26.8 | 29.7 | 14.9 | 18.8 |

TABLE 17

| | COATING #5 - Table 6 % COATING: 1.4% total tablet weight | | | | | | | | |
|---|---|---|---|---|---|---|---|---|---|
| FORMULA | A-3 | B-3 | C-3 | D-3 | E-3 | F-3 | G-3 | H-3 | I-3 |
| SORBITOL | 20% | 20% | 20% | 20% | 14% | 14% | 14% | 14% | 17% |
| CMC | 2% | 2% | 0% | 0% | 2% | 2% | 0% | 0% | 1% |
| AVICEL | 65% | 55% | 65% | 55% | 65% | 55% | 65% | 55% | 60% |
| SiO2 | 0% | 0% | 0% | 0% | 0% | 0% | 0% | 0% | 0% |
| ACDISOL | 4% | 4% | 4% | 4% | 4% | 4% | 4% | 4% | 4% |
| LACTOSE | 9% | 19% | 11% | 21% | 15% | 25% | 17% | 27% | 18% |
| TOTALS | 100% | 100% | 100% | 100% | 100% | 100% | 100% | 100% | 100% |

TABLE 18

| | COATING #5 - Table 6 % COATING: 1.4% total tablet weight | | | | |
|---|---|---|---|---|---|
| | COATING | % SPLITTING | | % RELEASE | |
| FORMULA (TABLE 17) | FAILURE (hrs) | @ 30 (minutes) | @ 60 | @ 60 (minutes) | @ 120 |
| A | 0.57 | 86.70 | 88.30 | 56.70 | 63.30 |
| B | 0.83 | 73.30 | 88.30 | 43.30 | 46.70 |
| C | 0.50 | 88.30 | 88.30 | 69.30 | 89.30 |
| D | 0.71 | 78.30 | 85.00 | 70.00 | 78.30 |
| E | 0.66 | 88.30 | 91.70 | 66.70 | 73.30 |
| F | 0.86 | 86.70 | 90.00 | 38.30 | 40.00 |
| G | 0.30 | 88.30 | 91.70 | 80.00 | 86.70 |
| H | 1.00 | 86.70 | 86.70 | 53.30 | 60.00 |
| I | 0.89 | 88.30 | 90.00 | 63.30 | 66.70 |
| AVE. | 0.7 | 85.0 | 88.9 | 60.1 | 67.1 |

THEORETICAL MODEL FOR PERMEABILITY-CONTROLLED EMBODIMENTS

The tablets (herein defined as drug-containing core with permeability-controlled coating) are assumed to be spherical with a displaceable volume, $V_d$, in the core due to the presence of a low bulk density solid (e.g., fumed silica) or a lipid material (e.g., mineral oil). The coating has a hydraulic permeability (to water) $L_p$ and reflection coefficient $\sigma$ (degree of permselectivity of the membrane). Water diffusion into the tablet core due to an osmotic pressure gradient displaces volume $V_d$ and then exerts a pressure (or stress) on the coating. When the critical stress $S^*$ is reached, the coating film breaks releasing the contents of the drug-containing core in a pulse dose. The variables that effect the polymer film properties alter the pulse time ($T_p$) through alteration of $L_p$, $\sigma$ and $S^*$ and the critical strain $e^*$.

The volume flux of water, $J_v$, into the tablet is given by:

$$J_v = L_p \cdot (\Delta P + \sigma \cdot \Delta \pi) \quad (1)$$

where $\Delta P$ and $\Delta \pi$ are the hydrostatic and osmotic pressure differences across the film. Assuming $\Delta P << \Delta \pi$ and that the density of water is approximately 1 g/cm³, $$\delta V / \delta t = A \cdot \sigma \cdot L_p \cdot \Delta \pi \quad (2)$$

where A is the surface area of the film. Assuming $L_p$ is constant, $$V - V_o = \Delta V = (A \cdot \sigma \cdot L_p \cdot \Delta \pi) \cdot t \quad (3)$$

for a very brittle film with a very low critical strain ($e^* < 1\%$) the coating films will fail when:

$$\Delta V = V_d \quad (4)$$

hence:

$$V_d = A \cdot \sigma \cdot L_p \cdot \Delta \pi \cdot T_p \quad (5)$$

or $$T_p = \frac{V_d}{A \cdot \sigma \cdot L_p \cdot \Delta \pi} \quad (6)$$

hence the pulse time $T_p$ is directly proportional to the displaceable volume and inversely proportional to A, $\sigma$, $L_p$ and $\Delta \pi$. $L_p$ in turn will be a function of film thickness, plasticizer content and processing variables.

For a film with a critical strain $e^* > 1\%$, the mechanical properties of the film must be considered. $S^*$ and $e^*$ are the critical stress and strain at failure of the film in tension. When $\Delta V$ due to water influx exceeds $V_d$, the resulting pressure will cause the film to expand. The film will break when the tablet has expanded to a new volume, $V_e^*$, such that the critical strain value for the film has been exceeded. For a spherical tablet:

$$r_e^* / r_o = (V_e^*/V_o)^{\frac{1}{3}} \quad (7)$$

where $r_e^*$ and $r_o$ are the expanded and initial radius and $V_o$ is the initial volume. Hence:

$$\Delta r^*/r_o = \frac{r_e^* - r_o}{r_o} = (V_e^*/V_o)^{\frac{1}{3}} - 1 \quad (8)$$

Since the tablets are not spherical and the films may not be of uniform thickness, the stress distribution across the film on the tablet will be different from that of a film in tension. Most coating films have been observed to fail at the edges, a result which is attributed to stress concentration and surface tension effects during film formation which cause the coating film to be thinner at the corners. However, the critical radius increase, $\Delta r^*/r_o$, at failure will be correlated with the critical strain ($e^*$) of a film in tension, $$\Delta r^*/r_o = a \cdot e^* = (V_e^*/V_o)^{\frac{1}{3}} - 1 \quad (9)$$

where a is a constant, or $$V_e^* = V_o \cdot (a \cdot e^*)^3 \quad (10)$$

Hence the film will fail when the water volume influx equals $V_f$, $$V_f = V_e^* + V_d \quad (11)$$

and analogous to equation 6, the pulse time $T_p$:

$$T_p = \frac{((a \cdot e^*)^3 - 1) \cdot V_c + V_d}{A \cdot a \cdot L_p \cdot \Delta\pi} \quad (12)$$

Equation 12 assumes that the osmotic pressure in the tablet core is high enough to break the film. Referring to the specific embodiments given herein, the mean tensile strength of cellulose acetate (CA 398-10) is 3300 psi and the estimated critical pressure value for a spherical film is approximately 350 psi. The osmotic pressure of a saturated sodium chloride solution is 5250 psi, approximately 15 times the pressure needed to cause film failure.

Equation 6, while not accounting for the time dependence of $e^*$, $L_p$ and A can still be used as a guide. Thus, the film properties, formulation and processing variables are the most critical variables and will effect $T_p$ through $e^*$ and $L_p$. The variables $\Delta\pi$ and $V_d$ are controlled by core design, type and amount of osmotic agent and amount of displaceable volume through use of colloidal silica dioxide of very low bulk density (0.03 g/cm$^3$) or mineral oil.

The theoretical analysis is based on measured tensile properties of the films. Based on the additional variables in tablet coating and differences between tensile properties and the stress distribution across a film on a tablet, it is desirable to establish a correlation between tensile and bulk properties, specifically the correlation between $e^*$ and $V_e^*$ (Equation 10).

For a film with a critical strain $e^* > 1\%$, the mechanical properties of the film must be considered. By combining Equations 11 and 12:

$$T_p = \frac{V_e^* + V_d}{A \cdot a \cdot L_p \cdot \Delta\pi} \quad (13)$$

where at any time, t, the change in volume, $V_e + V_d$, can be expressed as follows:

$$V_e + V_d = A \cdot a \cdot L_p \cdot \Delta\pi \cdot t \quad (14)$$

By following both the increase in mass and volume of the tablet with time it is possible to measure $V_e$ through the increase in volume of the tablet and to estimate $V_d$ by the difference in volume as calculated by change in mass and the actual increase in tablet volume $V_e$.

$$V_e = K \cdot (\pi_i(t) - \pi_e) \cdot t - V_d \quad (15)$$

where K is a constant ($K = A \cdot a \cdot L_p$) and $\Delta\pi$ can be expressed by $\pi_i(t) - \pi_e$ where $\pi_i(t)$ is the osmotic pressure inside the tablet core as a function of time and $\pi_e$ is the external osmotic pressure of the test media. The osmotic pressure in the core will remain constant until the concentration of the osmotic agent in the core falls below solubility at which time, $\pi_i$ will decrease due to dilution.

For concentrated solutions, the osmotic pressure can not be calculated directly from concentration due to activity coefficient changes with concentration. An empirical function can be fit to osmotic pressure concentration data (Handbook of Chemistry and Physics)

$$\pi(C) = a \cdot C + \beta \cdot C^2 + \delta \cdot C^3 \quad (16)$$

In the tablet core $C = C_s$ until $V_s$ (volume of a saturated solution in the core is reached) subsequently, $$\pi C(t) = M_o/V(t) \quad (17)$$

where $M_o$ is the initial mass of sodium chloride in the core. Equations 16 and 17 can then be combined with Equations 13-15 to account for time dependent core osmotic pressure changes.

By monitoring both changes in volume of the tablet and weight increases as a function of time, K and $\pi_i(t)$ can be determined through non-linear regression. By determining the pulse time, $T_p$, the value for critical volume $V_e^*$ inside the tablet at failure can be determined. By varying $\pi_e$, the external osmotic pressure of the test media and pre-soaking tablets in saturated sodium chloride solution for varying lengths of time to cause time dependent changes in the $L_p$, hydraulic permeability, (without a change in volume in the tablet core) an estimate of the time dependent changes in $L_p$ can be made. The volume at film failure $V_e^*$ can then be correlated with $e^*$ from the critical stress strain measurements (Equation 10).

By optimizing the formulation and process variables by application of the principles of the invention, it is possible to control the physical and mechanical properties of the films which in turn controls the pulse time and rate of release from the delivery system.

IN VIVO STUDIES AND DEMONSTRATION OF EFFICACY

A. Formulation of a Polymer Coated Dosage Form

The following is the formula for the tablet cores which were used for a 80 mg polymer-coated dose:

| INGREDIENT | AMOUNT (mg) |
|---|---|
| propranolol HCL | 80 |
| citric acid anhydrous | 60 |
| lactose hydrate | 28 |
| Avicel pH 102 | 120 |
| AcDiSol | 12 |
| TOTAL WEIGHT | 300 |

The tablet cores were produced on a Carver press with a ⅜th inch die and deep-cup concave punches, compressed at a pressure of 1600 lbs with a dwell time of 60 seconds.

The following formula was used for the polymer coating on the above-described core:

| INGREDIENT | AMOUNT |
|---|---|
| methylene chloride | 25 ml |
| methanol | 25 ml |
| cellulose acetate phthalate | 2.7 g |
| diethyl phthalate | 0.7 g |
| sudan red | 90 mg |

The coating solution was prepared and sprayed onto the tablet cores in a small coating drum rotated at ~13 RPM. Warm air was used to dry the coating on the tablets. After the coating was completed, the tablets were dried in an oven (50° C. to 60° C.) overnight. The weight of the coating was approximately 13 mg/tablet.

B. Dissolution Testing of the Polymer-Coated Dosage Form

Dissolution testing was performed to demonstrate that the coating would withstand transit through the acidic pH environment of the stomach.

Three coated tablets were placed in a standard USP dissolution apparatus (rotating basket) operated at 100 RPM. Simulated gastric fluid was used for the first two hours. At the end of two hours the solution was sampled and the tablets were immersed in simulated intestinal fluid (without enzymes) and the dissolution test continued. Samples were then taken every 30 minutes. Solutions were assayed by UV at 289 nm.

The dissolution test results indicated that the coating withstood two hours in the simulated gastric fluid. The average (three determinations) dissolution time in simulated intestinal fluid is as follows:

| TIME (minutes) | PERCENT DISSOLVED |
|---|---|
| 30 | 41 +/− 48 |
| 60 | 61 +/− 35 |
| 90 | 84 +/− 25 |

C. In Vivo Testing of the Immediate Release and Polymer Coated Dosage Forms

Single IV doses were given to each of a group of four beagle dogs: 5 mg of propranolol free base was dissolved in 3 ml sterile sodium chloride solution USP. The solution was infused over a 20 second period through an in-line millipore filter. Blood samples (1 ml) were withdrawn at desired intervals postinfusion. The plasma samples were analyzed and the results were recorded in plasma level time plots as shown in FIGS. 4 to 7. The IV results are shown as a "●." Similarly, blood plasma samples were withdrawn and analyzed for oral administration of 80 mg propranolol in immediate release form ("○") and the polymer coated dosage delivery form of section A. above ("+").

In other studies, an immediate release dosage form (INDERAL 80 mg) and the polymer-coated dosage form were orally administered separately to a group of four beagle dogs. The dosage forms were administered with 50 ml of water and monitored using a radiotelemetric system (Heidelberg capsule) in order to determine both the gastric emptying time (GET) and, in the case of the polymer-coated dosage form, the in vivo coating dissolution time (CDT) and the duration of tablet dissolution (DDT). FIGS. 8 to 11 are graphical plots of the pH-time profile in the gastrointestinal tract after administration of the polymer-coated dosage form. DDT is indicated by the release of citric acid from the drug-containing core which causes a spike in the pH time profile. The pH will remain depressed for the duration of the dissolution of the citric acid.

Blood samples (1 ml) were withdrawn at 5, 10, 15, 20, 30, 40, 50, 60, 70, 80, 90, 105, 120, 150, 180, 240, 300, 360 and 420 minutes after dosing for the immediate release dosage form. For the polymer coated tablets, the sampling schedule began at the time of coating dissolution (CDT). After dissolution, blood samples (1 ml) were withdrawn at 5, 15, 30, 45, 60, 90, 120, 190, 240, 300, 360 and 420 minutes. The plasma samples were assayed for free propranolol and the results are tabulated in Table 19:

TABLE 19

|  | DOG #1 | DOG #2 | DOG #3 | DOG #4 |
|---|---|---|---|---|
| IV (5 mg) | | | | |
| AUC (ng/ml.min) | 8176 | 10105 | 14691 | 14415 |
| half-life (min) | 118 | 130 | 101 | 110 |
| PO (INDERAL-80 mg) | | | | |
| AUC (ng/ml.min) | 9607 | 7005 | 23063 | 6206 |
| half-life (min) | 83 | 190 | 136 | 174 |
| bioavailability (% IV) | 7.3 | 4.3 | 9.8 | 2.7 |
| gastric emptying time | 70 | 150 | 60 | >420 |
| AUC (ng/ml.min) | 11348 | 5020 | 30622 | 8977 |
| half-life (min) | 112 | 137 | 154 | 159 |
| bioavailability (% IV) | 8.7 | 3.1 | 13 | 3.9 |
| gastric emptying time | 150 | >420 | 60 | 360 |
| PO (Polymer Coated 80 mg) | | | | |
| AUC (mg.ml.hr) | 8404 | 5097 | 17599 | 12995 |
| half-life (min) | 175 | 113 | 143 | 150 |
| bioavailability (% IV) | 6.4 | 3.2 | 7.5 | 5.6 |
| gastric emptying time | 250 | 180 | 32 | 171 |
| coating dissolution time | 20 | 37 | 31 | 19 |
| disintegration dissolution time | 17 | 50 | 17 | 17 |

After IV dosing, propranolol undergoes an initial distribution phase followed by a terminal phase with a half-life of ~120 minutes. After oral (PO) dosing with the immediate release dosage form (INDERAL-80 mg), the tablet rapidly dissolved and the blood levels of free propranolol also rapidly rose. Thus, bioavailability for the immediate release dosage form is affected primarily by the gastric emptying time (GET). The shorter the gastric emptying time, the greater the percentage of dose which is deposited into the duodenum as a bolus. With longer gastric emptying time, or no gastric emptying, the drug solution is slowly emptied into the duodenum and absorption is limited by the flow of drug out of the stomach. The faster the rate at which the drug is presented to the duodenum (rapid gastric emptying) the more rapidly the drug is absorbed and the higher the observed bioavailability.

With respect to the polymer coated dosage form of the present invention, the coating dissolution time (CDT) was between 20 and 40 minutes. The coating dissolution time was determined from the time of gastric emptying until the start of the disintegration/dissolution of the citric acid-containing core as shown by tracings of the gastrointestinal pH time profile shown in FIGS. 8 to 11. The disintegration dissolution time (DDT) was ~17 minutes in three of the dogs and about 50 minutes in the fourth. The blood levels of free propanolol, and consequently the bioavailability thereof, were affected by the disintegration dissolution time as evidence by the decreased bioavailability in the dog with the 50 minute DDT as compared to the other three dogs.

The average AUC and standard error for the two oral dosage forms are comparable and are shown below:

| immediate release | 12700 +/− 3200 ng/ml.min |
|---|---|
| polymer coated dosage form | 11000 +/− 2700 ng/ml.min |

Thus, these results demonstrate that the drug delivery system of the present invention can be tailored to simulate the AUC (preferably within 5%) of the immediate release dosage form administered in divided doses.

While the variability in the bioavailability occasioned with the immediate release dosage form is due to variability in the time of gastric emptying, the variability in bioavailability incurred with the polymer coated dosage form is due to the variability in the disintegration dissolution time. Since the variability in the disintegration dissolution time can be minimized by application of the principles of the invention, the variability of the pulsatile drug delivery system of the present invention is less than the variability of the immediate release dosage form.

It is to be understood that although the examples herein have been given in terms of propranolol, the principles of the invention are applicable to any other drug. The process of determining the effect of core contents and coating formulations, as set forth herein, will enable one of ordinary skill in the art to fabricate a pulsatile drug delivery system for any given drug and dosing schedule or combination of drugs and respective dosing schedules. The following is a list of drugs, having nonlinear kinetics, for which the invention herein is particularly advantageous. This list is merely illustrative, and in no way should be construed as limiting the scope of the invention:

Drugs With Nonlinear Kinetics

Aldosterone, Alprenolol, Amitryptyline, Aspirin, Beclomethasone Dipropionate, Bromocriptine Mesylate (F=0.6), Butorphanol Tartrate, Chlorpromazine HCl, Cimetidine (F=0.7), Codeine, Cortisone, Cyclobenzamine HCl, Desmethylimipramine, Dihydroergotamine Mesylate, Diltiazem HCl, Dobutamine HCl, Dopamine HCl, Epinephrine, Ergoloid Mesylates, Ergotamine Tartrate, Estradiol, Ethinylestradiol (F=0.4), Flunisolide, Fluorouracil, 5-Fluoro-21-Deoxyuridine, Guanethidine Sulfate, Hydralazine HCl, Imipramine HCl, Isoethorine HCl & Mesylate, Isoproterenol Sulfate, Isosorbide Dinitrate, Levallorphan Tartrate, Lidocaine HCl, Meperidine HCl, 6-Mercaptopurine, Metapoterenol Sulfate, Methoxamine HCl, Methylprednisolone (F=0.85), Methyltestosterone, Metoprolol Tartrate, Morphine Sulfate, Nalbuphine HCl, Naloxone HCl, Neostigmine, Nifedipine, Nitroglycerin, Norepinephrine Bitartrate, Norethindrone (F=0.65), Nortriptylene HCl, Oxprenolol, Oxyphenbutazone, Penicillamine, Pentazocine HCl & Lactate, Phenacetin, Phentolamine HCl & Mesylate, Phenylephrine HCl & Bitartrate, Prednisone (F=0.85), Progesterone, Propoxyphene HCl & Napsylate, Propranolol HCl, Ritodrine HCl, Salicylamide, Salbutamol, Testosterone, Timolol Maleate, and Verapamil HCl.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A drug delivery system for administering a drug in controlled pulse doses to an aqueous environment in the body of a living being, the drug delivery system comprising, in combination, a unitary body configured for administration to the body of the living being, the unitary body containing therein first and second subunits, each having a respective core portion for containing an individual dose of a drug, said first subunit having a respectively associated first coating portion formed of a first polymer material and said second subunit having a respectively associated second coating portion formed of a second polymer material, said first and second coating portions being arranged to surround their respective core portions and being substantially impermeable to the drug contained in said respective core portions, said first coating portion being characterized by a first predetermined period of core protection time during which release of the drug from its associated core portion is prevented after communication with the aqueous environment and said second coating portion being characterized by a second predetermined period of core protection time which differs from said first predetermined period of core protection time, the expiration of said respective periods of core protection time resulting in immediate release of the content of the respective core portions into the aqueous environment.

2. The drug delivery system of claim 1 wherein said first and second polymer materials are water permeable polymers, each having respective tensile strength and maximum elongation characteristics whereby the respective cohesive strength of the associated coating portion is exceeded after said respective periods of core protection time in response to water obtained from the aqueous environment penetrating said respective coating portion and traveling in an inward direction to create a pressurizing force in said respective core portion which causes said respectively associated coating portion to rupture after expiration of said respective periods of core protection time.

3. The drug delivery system of claim 2 wherein at least one of said first and second polymer materials is selected from the group of water permeable polymers consisting of cellulose acetate, ethyl acetate latexes, ethyl cellulose, cellulose butyrate, and methacrylic acid copolymers.

4. The drug delivery system of claim 3 wherein at least one of said first and second polymer materials is cellulose acetate.

5. The drug delivery system of claim 4 wherein at least one of said first and second polymer materials is further provided with a plasticizer.

6. The drug delivery system of claim 5 wherein said plasticizer is selected from the group consisting of polyethylene glycol, diethyl phthalate, and dibutyl phthalate.

7. The drug delivery system of claim 1 wherein at least one of said respective core portions is further provided with viscosity enhancers and disintegrants.

8. The drug delivery system of claim 1 wherein the aqueous environment has predetermined pH characteristics, said first and second polymer materials are pH-responsive materials, each being soluble in an aqueous environment having a respective predetermined pH, whereby said respective coating portion dissolves after expiration of the respective periods of core protection time in response to a pH characteristic of the aqueous environment.

9. The drug delivery system of claim 8 wherein at least one of said first and second pH-responsive materials is selected from the group consisting of cellulose acetate phthalate, methylcellulose phthalate, hydroxyethylcellulose, cellulose acetate tetrahydrophthalate, cellulose acetate hexahydrophthalate, methyl-methacrylate, methacrylic acid, and combinations thereof.

10. The drug delivery system of claim 9 wherein said pH-responsive material is a layered combination of cellulose acetate phthalate, and a mixture of methylmethacrylate and methacrylic acid.

11. The drug delivery system of claim 1 wherein said unitary body is configured as a tablet.

12. The drug delivery system of claim 1 wherein said unitary body is configured as a capsule.

13. The drug delivery system of claim 1 wherein the drug is a first-pass metabolized drug.

14. The drug delivery system of claim 13 wherein the first-pass metabolized drug is propranolol.

15. The drug delivery system of claim 1 wherein there is further provided at least a third subunit having a core portion for containing an individual dose of the drug, said third subunit having a coating portion formed of a third polymer material being characterized by a third predetermined period of core protection time.

16. The drug delivery system of claim 15 wherein there are further provided additional subunits in said unitary body, the total number of subunits comprising a whole number less than or equal to ten, each subunit having a respective core portion for containing an individual dose of drug and a respective coating portion formed of a respective polymer material being characterized by respective predetermined periods of core protection time.

17. The drug delivery system of claim 8 wherein said first and second pH-responsive materials comprise respective weight percentages $E_1$ and $E_2$ of a pH-responsive polymeric material in a solvent, said first and second pH-responsive polymeric materials being cured at respective temperatures $T_1$ and $T_2$ for a given time period, the respective periods of core protection time, $T_{p1}$ and $T_{p2}$ being described by the equation:

$$T_p = -36.9 + 0.113T + 1.27E - 0.00197(T \cdot E),$$

where T is in °K.

18. The drug delivery system of claim 2 wherein said core portions contain viscosity enhancing agents in respective concentrations $N_1$ and $N_2$, and said first and second water permeable polymer materials further contain plasticizers in respective concentrations $P_1$ and $P_2$, said first and second water permeable polymer materials being cured at a temperature for a given time period, the respective periods of core protection time, $T_{p1}$ and $T_{p2}$ being described by the equation:

$$T_p = 8.3 + 0.064N - 0.312P + 0.0130(N \cdot P).$$

* * * * *